United States Patent [19]

Yamasaki et al.

[11] Patent Number: 5,516,672
[45] Date of Patent: May 14, 1996

[54] STABILIZED PEROXIDASE COMPOSITIONS AND ANTIBODY COMPOSITIONS

[75] Inventors: Masahiko Yamasaki; Morito Uemura; Shinya Yoshida, all of Tokyo, Japan

[73] Assignee: Konica Corporation, Tokyo, Japan

[21] Appl. No.: 109,985

[22] Filed: Aug. 23, 1993

Related U.S. Application Data

[63] Continuation of Ser. No. 552, Jan. 4, 1993, abandoned, which is a continuation of Ser. No. 343,209, Apr. 26, 1989, abandoned.

[30] Foreign Application Priority Data

Apr. 26, 1988 [JP] Japan .................................. 63-105168

[51] Int. Cl.$^6$ ............................ C12N 9/99; G01N 33/53; C07K 16/00
[52] U.S. Cl. .................................. 435/184; 435/4; 435/5; 435/28; 436/501; 530/387.1
[58] Field of Search ........................... 435/4, 5, 28, 184; 436/501; 530/387.1

[56] References Cited

U.S. PATENT DOCUMENTS

| | | | |
|---|---|---|---|
| 4,299,916 | 11/1981 | Litman et al. | 435/6 |
| 4,764,468 | 8/1988 | Wehner et al. | 435/188 |
| 4,921,791 | 5/1990 | Yamasaki et al. | 435/28 |

FOREIGN PATENT DOCUMENTS 61-239890  10/1986  Japan .
6463380  3/1989  Japan .

OTHER PUBLICATIONS

*Lange's Handbook of Chemistry* (Ed, N. A. Lange, McGraw-Hill Book Co., New York, NY, 1985) pp. 3-133 to 3-140.
Pathology and Clinical Medicine, vol. 6, pp. 13–15, 34–35, 77–78, and 279, Bunkodo Co. Ltd. (Pertinent portions are translated into English) (1988).
Pine, S. J., et al., Organic Chemistry, McGraw-Hill International Book Company, 4th Edition, pp. 620–625 (1981).
Badger, G. M., The Structures and Reactions of the Aromatic Compounds, Cambridge University Press, pp. 204–208 (1954).
Wiberg, K. B., Organic Chemistry, John Wiley & Sons, Inc., pp. 278–183 (1964).
Chemical Abstracts, vol. 105:38764b, (1986).

*Primary Examiner*—W. Gary Jones
*Assistant Examiner*—Ardin H. Marschel
*Attorney, Agent, or Firm*—Finnegan, Henderson, Farabow, Garrett & Dunner

[57] ABSTRACT

Disclosed are a peroxidase composition and an antibody composition with high stability. In the compositions of the present invention, a substituted benzene ring having at least one hydroxyl group and at least one substituting group selected from the group consisting of groups with a Hammett sigma value σ p of not more than −0.20, groups with a Hammett sigma value σ p of not less than +0.24 and amide group is contained as a stabilizer for stabilizing the activity of peroxidase or the antibody.

13 Claims, No Drawings

STABILIZED PEROXIDASE COMPOSITIONS AND ANTIBODY COMPOSITIONS

This application is a continuation of application Ser. No. 08/000,552, filed Jan. 4, 1993, now abandoned, which is a continuation of application Ser. No. 07/343,209, filed Apr. 26, 1989, now abandoned.

BACKGROUND OF THE INVENTION

1. Field of the Invention

This invention relates to a peroxidase composition and to an antibody composition used in the field of diagnosis.

2. Description of the Related Art

Recently, in the field of clinical examination and diagnosis, measurement of various substances utilizing an immunological reaction and/or an enzyme reaction is widely performed.

Peroxidase is an enzyme which catalyzes the oxidation of various substances utilizing hydrogen peroxide as a hydrogen acceptor. Since peroxidase can be utilized for coloring reactions in which a color generator is oxidized by peroxidase to form a pigment, peroxidase is now more and more widely used as an enzyme marker for immunoassay and is used for the determination of hydrogen peroxide generated in an oxidation reaction of a target substance oxidized with the corresponding oxidase so as to quantify the target substance. However, peroxidase has poor stability, especially in the form of a liquid composition at a level of not more than several µg/ml which is employed in practice, and it is very difficult to maintain activity when the liquid composition is stored at room temperature for a long time. Further, it is known that the activity of the peroxidase is largely reduced when the peroxidase composition is lyophilized.

On the other hand, various antibody compositions are now widely used in the field of immunoassay. It is also known that the activity of the antibody is reduced with time especially when the level of the antibody in the composition is low. This phenomenon occurs more severely when the storage temperature of the composition is higher.

Thus, it is difficult to store the peroxidase composition and antibody composition for a long time, and it is a serious problem for quality control of the composition used as a reagent for measurement or as a reagent for diagnosis. Therefore, the stabilization of the compositions is strongly demanded. In particular, as for the peroxidase-labelled antibody which is a conjugate of peroxidase and an antibody, in order to eliminate the possibility that a stabilization method for one component adversely affects the stability of another component, a stabilization method effective for the stabilization of both the peroxidase and the antibody is desired.

SUMMARY OF THE INVENTION

Accordingly, the object of the present invention is to provide a peroxidase composition having improved stability.

Another object of the present invention is to provide an antibody composition having improved stability.

The present inventors have intensively investigated the method for stabilization of peroxidase composition and antibody composition to find that by adding a specific benzene derivative as a stabilizer to the peroxidase composition or to the antibody composition, the stability of the compositions is largely improved.

That is, the present invention provides a peroxidase composition comprising peroxidase and a substituted benzene ring having at least one hydroxyl group and at least one substituting group selected from the group consisting of groups with a Hammett sigma value σ p of not more than −0.20, groups with a Hammett sigma value σ p of not less than +0.24 and the amide group.

The present invention further provides an antibody composition comprising an antibody and a substituted benzene ring having at least one hydroxyl group and at least one substituting group selected from the group consisting of groups with a Hammett sigma value σ p of not more than −0.20, groups with a Hammett sigma value σ p of not less than +0.24 and amide group.

The peroxidase composition and the antibody composition of the present invention have high stability. Therefore, even if they are stored for a long time, the activity of the peroxidase or the antibody is not so lowered, so that the reliability of the compositions as reagents is affected. Since the peroxidase and the antibody is stabilized by the same stabilizer, the present invention is especially useful for stabilizing the peroxidase-labelled antibody.

DETAILED DESCRIPTION OF THE PREFERRED EMBODIMENTS

The peroxidase contained in the peroxidase composition of the present invention may be of any origin, that is, the peroxidase may be originated from plants, animals, microorganisms and so on. Examples of the peroxidase include horse radish peroxidase, lacto peroxidase, glutathione peroxidase, myelo peroxidase and cytochrome C peroxidase. Among these, horse radish peroxidase is especially preferred.

The peroxidase contained in the peroxidase composition of the present invention may be in the free form or in the form of a conjugate with a second substance. Further, the peroxidase may be in the form of a complex comprising the peroxidase and an antiperoxidase antibody.

As the second substance which may be conjugated with the peroxidase contained in the composition of the present invention, although any substance may be conjugated, an immunologically active substance is preferred. Examples of the immunologically active substance include antigens, antibodies, haptens and protein A. Examples of the antigens and haptens include proteins, carbohydrates, lipids, complex carbohydrates, polysaccharides, nucleic acids, enzymes, hormones, antibiotics, bacterial antigens, viral antigens, cancer antigens, avidin, biotin and the like.

The antibody contained in the antibody composition of the present invention may be that prepared by immunizing a mammal such as rabbit, goat and mouse or a bird such as chicken with the above-mentioned antigen and by recovering the antibody from the serum of the animal. Or the antibody contained in the antibody composition may be a monoclonal antibody obtained from a hybridoma prepared by cell hybridization technique or from a plasma cell transformed with a virus. The antibody may be a fragment such as Fab and $F(ab')_2$.

The antibody contained in the antibody composition of the present invention may also be in the form of a conjugate with a second substance such as a labelling substance and an immunologically active substance. Examples of the labelling substance include radioisotopes, enzymes such as peroxidase, alkaline phosphatase and β-galactosidase, fluorescent substances, luminescent substances, biotin, avidin, chelates, metal colloids and toxins. Examples of the immunogically active substance include antigens, antibodies and haptens.

The binding of the peroxidase with the second substance, as well as the binding of the antibody with the second substance may be carried out by the conventional method well-known in the art utilizing a physical bond such as adsorption or a chemical bond such as ionic bond and covalent bond. Among these, the covalent bond is most preferred. Forming the covalent bond between the peroxidase or the antibody and the second substance may be attained by conventional methods well-known in the art. For example, glutaraldehyde may be employed as a crosslinking agent to form a crosslinkage between amino groups, or the aldehyde group generated by the treatment of the sugar chain of the peroxidase with periodic acid may be bonded with an amino group of the second substance.

The substituted benzene ring contained as a stabilizer in the peroxidase composition or in the antibody composition of the present invention has at least one hydroxyl group and at least one substituting group selected from the group consisting of groups with a Hammett sigma value σ p of not more than −0.20, preferably −0.90 to −0.20, groups with a Hammett sigma value σ p of not less than +0.24, preferably +0.24 to +0.80, and the amide group.

The definition of the Hammett sigma value σ p and the list of the Hammett sigma values of various groups are known and are described, for example, in Lange's Handbook of Chemistry (McGraw-Hill Book Company).

Preferred examples of the substituting group with a Hammett sigma value σ p of not more than −0.20 may include those represented by the formulae —$OR^1$, —$NHR^1$, —$NR^1R^2$ or —OH. Preferred examples of the substituting group with a Hammett sigma value σ p of not less than +0.24 may include those represented by the formulae —$COR^1$, —$COOR^1$, —$CONHR^1$, —$CONR^1R^2$, —COOH, —$CONH_2$, —$SO_2R^1$, —$SOR^1$, —$SO_2NH_2$, —$SO_3H$ and —$NO_2$. Preferred examples of the amide group may include one represented by the formula —$NHCOR^1$. Among these, especially preferred are those represented by the formulae —$OR^1$, —$COR^1$, $COOR^1$, —COOH, —$CONHR^1$, —$CONH_2$ and —$NHCOR^1$. Among these, the most preferred is —$OR^1$.

In the formulae just mentioned above, , $R^1$ and $R^2$, the same or different, represent an aliphatic hydrocarbon group, alicyclic group, aryl group or heterocyclic group. In cases where the benzene ring is substituted with two or more $R^1$ or $R^2$, the two or more $R^1$ or $R^2$ may be the same or different.

The aliphatic hydrocarbon group which may be the $R^1$ and/or the $R^2$ may be saturated or unsaturated, and may be straight or branched. Preferred hydrocarbon groups are alkyl groups (such as methyl, ethyl, propyl, isopropyl, butyl, t-butyl, isobutyl, dodecyl and octadecyl group) and alkenyl group (such as allyl and octenyl group).

The alicyclic group which may be the $R^1$ and/or the $R^2$ may preferably be a 5-membered or 6-membered ring, such as cyclopentyl and cyclohexyl group.

Preferred examples of the heterocyclic group which may be the $R^1$ and/or the $R^2$ may include pyridinyl, piradinyl, pyridadinyl, quinolyl, pyrrolidyl, furalyl, thienyl, piperidyl, pyrrolyl, pyrrolinyl, tetrazolyl, thiazonyl, imidazolyl, morpholyl, furyl, oxazolyl, thiazolyl, benzimidazolyl, benzoxazolyl and benzthiazolyl group.

Preferred example of the aryl group which may be the $R^1$ and/or the $R^2$ may include phenyl and naphthyl group.

The substituted benzene ring contained in the composition of the present invention as a stabilizer may contain one or more substituents in addition to the substitutent described above. Further, it is also possible that two substituents may form a second ring (non-aromatic or aromatic) which is fused with the benzene ring of the benzene derivative.

Preferred examples of the non-aromatic ring formed by the two substituents, which is fused with the benzene ring may include 5-membered and 6-membered rings such as cyclopentane ring, cyclohexane ring and cyclohexene ring.

Preferred examples of the aromatic ring formed by the two substituents, which is fused with the benzene ring may include 5-membered and 6-membered rings such as phenyl, pyridinyl, piradinyl, piridadinyl, pyrrolidyl, furalyl, thienyl, piperidyl, pyrrolyl, pyrrolinyl, thiadinyl, imidazolyl, furyl, oxazolyl and thiazolyl group.

The aliphatic hydrocarbon group, alicyclic group, aryl group and heterocyclic group, which are the $R^1$ or $R^2$, as well as the non-aromatic ring and the aromatic ring which is fused with the benzene ring and which is formed by the two substituents may contain one or more additional substituents.

Examples of such a substituent may include halogen such as chlorine and fluorine atom, nitro group, cyano group, hydroxyl group, keto group, carboxyl group, sulfo group, amino group (such as amino, alkylamino, dialkylamino, anilino and N-alkylanilino), alkyl group (such as methyl, propyl, isopropyl, t-butyl, octadecyl, cyanoalkyl, haloalkyl and aralkyl), alkenyl group, aryl group (such as phenyl, tolyl, acetylaminophenyl, 4-lauroylaminophenyl and ethoxyphenyl), heterocyclic group, alkoxyl group (such as ethoxy, phenoxy, methoxy and tetradecyloxy), aryloxy group (such as phenoxy, 2,4-di-t-amylphenoxy, p-t-butylphenoxy, 4-n-dodecyloxyphenoxy, 4-hydroxy-3-t-butylphenoxy, 4-hydroxy-3-n-butylphenoxy), arylthio group, amide group (such as acetoamide, methanesulfonamide, p-dodecylbenzene sulfonamide), carbamoyl group (such as N-p-carboxynaphthoxyphenylcarbamoyl, N,N-dihexylcarbamoyl, N-benzylcarbamoyl, N-ethylcarbamoyl and N-methoxyethylcarbamyol), sulfamoyl group (such as N,N-diethylsulfamoyl), alkylsulfonyl group, arylsulfonyl group (such as benzene sulfonyl and m-chlorobenzene sulfonyl), acyloxy group (such as acetyloxy and m-chlorobenzoyloxy), acyloxycarbonyl group and alkoxycarbonyl group (such as N-methoxyethyl carbamoylmethoxycarbonyl, ethoxycarbonyl, methoxycarbonyl and triethoxycarbonyl), aryloxy carbonyl group (such as phenoxycarbonyl and p-nitrophenoxycarbonyl), arylthiocarbonyl group (such as phenylthiocarbonyl) and imide group (such as succinimide and octadecylsucinimide).

Most preferred $R^1$ and $R^2$ are $C_1$–$C_4$ alkyl groups.

Preferred examples of the groups with a Hammett sigma value σ p of not more than −0.20 may include —$OCH_3$ (σ p= −0.27) (hereinafter, the value in parentheses indicates the Hammett sigma value), —$OC_2H_5$ (−0.24), —$OC_6H_5$ (−0.32), —OH (−0.37), —$NHCH_3$ (−0.84) and —$N(CH_3)_2$ (−0.44).

Preferred examples of the groups with a Hammett sigma value σ p of not less than +0.24 may include —$COCH_3$ (+0.50), —$COC_6H_5$ (+0.36), —$COOCH_3$ (+0.395) , —$COOC_2H_5$ (+0.45), —COOH (+0.41), —$CONH_2$ (+0.36) , —$SO_2CH_3$ (+0.68), —$SOCH_3$ (+0.49), —$SO_2NH_2$ (+0.62), and —$SO_3H$ (+0.50) and —$NO_2$ (+0.78).

Preferred examples of the amide group include —$NHCOCH_3$.

The substituted benzene ring of the present invention may be in the form of a salt. Examples of the salt include alkaline metal salts such as sodium salt and potassium salt; alkaline earth metal salts such as calcium salt and magnesium salt, organic salts such as ammonium salt and pyridinium salt, and acid addition salts such as sulfuric acid salt and hydrochloric acid salt, Two or more of the substituted benzene rings may be contained in the composition of the present invention, Preferred examples of the substituted benzene ring employed in the present invention may include those represented by the following formulae:

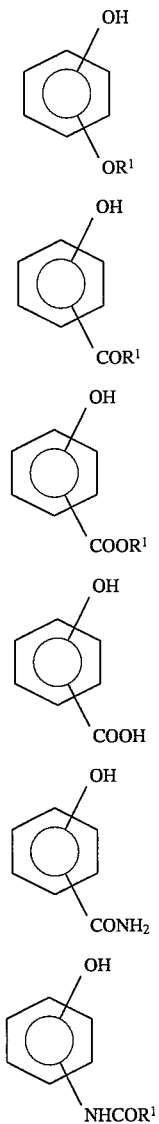

wherein $R^1$ represents the same meaning as mentioned above, The position of the substituting group is preferably in the para position with respect to the hydroxyl group.

Preferred examples of the substituted benzene ring contained in the composition of the present invention as a stabilizer may include hydroquinone monomethyl ether, hydroquinone monoethyl ether, hydroquinone monophenyl ether, o-methoxyphenol, o-ethoxyphenol, 2,6-dimethoxyphenol, hydroquinone, N-methyl-p-hydroxyaniline, N,N-dimethyl-p-hydroxyaniline, N-(p-hydroxyphenyl)glycine, p-hydroxyacetophenone, 2,4-dihydroxyacetophenone, p-hydroxybenzophenone, p-hydroxybenzoic acid, m-hydroxybenzoic acid, o-hydroxybenzoic acid, 2,3-dihydroxybenzoic acid, 2,4-dihydroxybenzoic acid, 2,5-dihydroxybenzoic acid, 2,6-dihydroxy benzoic acid, 3,4-dihydroxy benzoic acid, 3,5-dihydroxy benzoic acid, 2,3,4-trihydroxy benzoic acid, 2,3,5-trihydroxy benzoic acid, 3,4,5-trihydroxy benzoic acid, 4-hydroxy-3-methoxy benzoic acid, 4-hydroxy-3,5-dimethoxy benzoic acid, 4-hydroxy phthalic acid, 2-hydroxy terephthalic acid, methyl p-hydroxybenzoate, ethyl p-hydroxybenzoate, n-propyl p-hydroxybenzoate, ethyl 3,4-dihydroxy benzoate, p-hydroxybenzamide, p-hydroxybenzoylethylamine, 1-naphthol-2-carboxylic acid, 3-naphthol-2-carboxylic acid, p-hydroxyacetoanilide, p-hydroxybenzenesulfinyl methane, p-hydroxybenzene sulfonamide, p-sulfonylphenol and p-nitrophenol.

The peroxidase composition and the antibody composition of the present invention may be in any form such as powder and solution. In cases where the composition is in the form of a solution, the preferred content of the stabilizer is, although it varies depending on the nature and the content of the peroxidase or the antibody, usually about 0.005 - about 500 mM, more preferably about 0.01 - about 50 mM. In cases where the composition is in the form of a powder prepared by the lyophilization of a solution containing the peroxidase or the antibody, a solution containing the peroxidase or the antibody in the amount as mentioned above is preferably lyophilized.

To further promote the stability of the peroxidase or the antibody in the composition of the present invention, serum of animals such as horse serum, bovine serum, sheep serum, rabbit serum and human serum, or a component thereof such as bovine serum albumin and human serum albumin may be incorporated in the composition of the present invention. In cases where the composition is in the form of a solution, the content of the serum may preferably be 1–50 (v/v) %, and the content of the serum component may preferably be 0.1–5 (w/v) %.

Further, if desired, the composition of the present invention may contain a water-soluble macromolecule such as proteins including gelatin, egg albumin and casein, and polyalkyleneglycol for the purpose of obtaining further superior effect. A carbohydrate such as sucrose may also be added to the composition for the purpose of promoting the advantageous effect of the present invention. An antiseptic such as thimerosal may also be added to the composition for preventing the putrefaction of the composition.

The composition of the present invention may optionally further contain a buffer and a salt such as sodium chloride. Buffers typically used in this field such as Tris buffers, phosphate buffers, carbonate buffers and acetate buffers may be employed, which give a pH of 4–9 in the case of peroxidase composition and a pH of 3–11 in the case of antibody composition.

The order of adding the components when formulating the composition in the form of a solution does not matter at all.

The peroxide composition and the antibody composition of the present invention may be used in the conventional manner well-known in the art.

The activity of the peroxidase may be measured according to the conventional method by contacting the peroxidase composition of the present invention, hydrogen peroxide and a substrate which as a color generator such as o-phenylenediamine and by measuring the degree of the enzyme reaction. In cases where the substrate is a color generator, this measurement may be conducted by measuring the absorbance of the generated pigment.

The activity of the antibody may also be conducted in accordance with the conventional method well-known in the art. Thus, agglutination method, competition method, sandwich method and ELISA method which are well-known in the art may be employed. In one example, a target labelled antibody and the corresponding antigen fixed to a carrier are reacted and the amount of the label fixed to the carrier is measured to determine the amount of the antibody.

The stability of the activity of the peroxidase or the antibody may be evaluated by measuring the activity at a plurality of time points or by comparing the activities of the peroxidase or the antibody in the composition held at 4° C. and 37° C.

With the peroxidase composition of the present invention, the decreased the activity of the peroxidase is reduced when the composition is stored for a long time or stored at room temperature. The reduction of the activity of peroxidase is also prevented when the peroxidase composition is lyophilized. The antibody composition of the present invention also excells in storage stability. Since the benzene derivative contained in the composition as a stabilizer is effective for both the peroxidase and the antibody, the stabilizer is especially effective as a stabilizer of peroxidase-labelled antibodies. Since the composition of the present invention has a high stability, when the composition is used as a reagent for immunoassay, the reagent is very useful in the field of clinical examination and diagnosis.

The present invention will now be described by way of examples thereof. It should be noted that the examples are presented for illustration purposes only and should not be interpreted in any restrictive way.

EXAMPLE 1

A solution containing 1 µg/ml of horse radish peroxidase and 5 mM of hydroquinone monomethyl ether as a stabilizer in phosphate buffer saline (hereinafter referred to as "PBS") was prepared. For comparison, a solution which did not contain the stabilizer was also prepared. Each solution was held at 4° C. or 37° C. and the enzyme activity was monitored with time. The enzyme activity was measured by adding 2 µl of the aliquot of the above-mentioned sample composition, which is 10-fold diluted with PBS to 500 µl of citrate-phosphate buffer (pH 4.9) containing 2 mg/ml of o-phenylenediamine and 0.02 w/v% of hydrogen peroxide, allowing the resulting mixture at 37° C. for 30 minutes, adding 2 ml of 1N sulfuric acid and then measuring the absorbance at 492 nm. The measurement of the enzyme activity was conducted in this manner in the other Examples. The enzyme activity immediately after the preparation of the sample is defined as 100%, and the change in the enzyme activity with time is shown in Table 1.

TABLE 1

| Temperature | Conc. of Stabilizer | Enzyme Activity (%) Days Stored | | |
|---|---|---|---|---|
| | | 0 | 2 | 6 |
| 4° C. | 5 mM | 100 | 51 | 12 |
| 4° C. | not added | 100 | 20 | <0.05 |
| 37° C. | 5 mM | 100 | 27 | 4 |
| 37° C. | not added | 100 | 3 | <0.05 |

It is apparent from Table 1 that the benzene derivative defined in the present invention is effective for the stabilization of peroxidase.

EXAMPLE 2

A solution containing 10 µg/ml of peroxidase-bound anti-GT-II monoclonal antibody and 5 mM of hydroquinone monomethyl ether as a stabilizer in PBS was prepared. For comparison, a solution which did not contain the stabilizer was also prepared. Each solution was held at 4° C. or 37° C. for 1 week and then diluted with PBS containing 1 w/v% of BSA and 5 w/v% of horse serum to a final concentration of 200 ng/ml. Using the resulting solution as the secondary antibody, the enzyme stability, the secondary antibody stability and the antibody stability were determined as follows:

The horse radish peroxidase-bound GT-II monoclonal antibody was prepared by conjugating monoclonal antibody 3872 described in Japanese Patent Disclosure (Kokai) No. 174100/87 (ATCC HB8945) with horse radish peroxidase and purifying the resulting conjugate in accordance with the method described in J. Immu. Meth. 30, 246–255, 1979.

Anti-galactosyltransferase isoenzyme II (hereinafter referred to as "GT-II", monoclonal antibody with a concentration of 10 µg/ml was fixed on polystyrene beads at 4° C. overnight, and then the beads were blocked with 1 w/v% BSA-PBS. The resulting beads were then reacted with human ascite fluid at 21° C. overnight and the resultant was washed with PBS, followed by being allowed to react with the secondary antibody at 21° C. for 2 hours. After the reaction, the beads were washed with PBS and the enzyme activity of the beads was determined, which is defined as the activity of the secondary antibody. The stability of the secondary antibody is expressed in terms of the percentage of the activity of the secondary antibody held at 37° C. to that of the secondary antibody held at 4° C. Further, the enzyme activity of the secondary antibody was determined as in Example 1 and the enzyme stability was expressed in terms of percentage. The stability of the antibody is expressed in terms of percentage of the stability of the secondary antibody to the stability of the enzyme activity.

The results are shown in Table 2.

TABLE 2

| Hydroquinone Monomethyl Ether | Stability (%) | | |
|---|---|---|---|
| | Enzyme | Sec. Ab* | Ab |
| 5 mM | 84 | 71 | 84 |
| not added | 77 | 2 | 3 |

Ab*: Antibody

It can be seen from Table 2 that the antibody composition containing the substituted benzene ring defined in the present invention has improved antibody stability.

EXAMPLE 3

To 20 mM phosphate buffer (pH 7.4), containing 1 w/v% of bovine serum albumin (hereinafter referred to as "BSA") and 100 mM sodium chloride, horse radish peroxidase was added to a final volume of 100 ng/ml and then hydroquinone monomethyl ether as a stabilizer was added in the amount shown in Table 3. Each solution was kept at 4° C. or 37° C., and the enzyme activity was measured on day 0, day 7 and day 14 from the preparation of the solution. The enzyme stability is expressed by the percentage of the enzyme activity of the composition kept at 37° C. to that of the composition kept at 4° C.

The enzyme activity was determined as in Example 1. The results are shown in Table 3 below.

TABLE 3

| Hydroquinone Monomethyl Ether | Enzyme Stability (%) Days Stored | | |
|---|---|---|---|
| (mM) | 0 | 7 | 14 |
| 50 | 100 | 98 | 98 |
| 10 | 100 | 98 | 96 |
| 1 | 100 | 97 | 95 |
| 0.1 | 100 | 90 | 82 |
| 0.01 | 100 | 71 | 32 |
| not added | 100 | 19 | 4 |

It is apparent from Table 3, that the peroxidase compositions containing the hydroquinone monomethyl ether have increased stability.

EXAMPLE 4

To 1 w/v% of PBS, horse radish peroxidase-bound anti-galactosidase isozyme II monoclonal antibody was added to a final concentration of 200 ng/ml and then ethyl p-hydroxybenzoate as a stabilizer was added in the amount shown in Table 4 below. The enzyme activity was determined as in Example 1. The results are shown in Table 4.

TABLE 4

| Ethyl p-hydroxybenzoate | Enzyme Stability (%) Days Stored | | |
|---|---|---|---|
| (mM) | 0 | 7 | 14 |
| 5 | 100 | 96 | 95 |
| 1 | 100 | 96 | 92 |
| 0.1 | 100 | 95 | 90 |
| 0.01 | 100 | 80 | 67 |
| not added | 100 | 18 | 4 |

From Table 4, it is apparent that the stability of the peroxidase is promoted if the peroxidase composition contains ethyl p-hydroxybenzoate even if the peroxidase is contained in the form of a conjugate.

EXAMPLE 5

Various benzene derivatives were employed as the stablizer and the enzyme stability was checked as in Example 4 using the peroxidase-bound antibody. In this example, the enzyme activity was measured on day 7. The results are shown in Table 5.

TABLE 5

| Benzene Derivatives | Concentration (mM) | Stability (%) |
|---|---|---|
| Hydroquinone Monoethyl Ether | 3 | 100 |
| Hydroquinone Monophenyl Ether | 0.5 | 97 |
| o-methoxy Phenol | 3 | 93 |
| o-ethoxy Phenol | 3 | 95 |
| 2,6-dimethoxy Phenol | 3 | 99 |
| Hydroquinone | 3 | 90 |
| Not Added | — | 17 |

As is apprent from Table 5, various benzene derivatives defined in the present invention are effective for the stabilization of peroxidase.

EXAMPLE 6

Various benzene derivatives were added to the peroxidase-bound antibody described in Example 4 in the amount of 3 mM and the enzyme stability was checked on day 10. The results are shown in Table 6.

TABLE 6

| Benzene Derivatives | Stability (%) |
|---|---|
| p-hydroxy Benzoic Acid | 95 |
| m-hydroxy Benzoic Acid | 78 |
| 2,4-dihydroxy Benzoic Acid | 95 |
| 2,5-dihydroxy Benzoic Acid | 94 |
| 3,4-dihydroxy Benzoic Acid | 89 |
| 3,4,5-trihydroxy Benzoic Acid | 78 |
| 4-hydroxy-3,5-dimethoxy Benzoic Acid | 98 |
| 4-hydroxy Phthalic Acid | 38 |
| 3-naphthol-2-carboxylic Acid | 95 |
| Not Added | 7 |

It can be seen from Table 6 that the benzene derivatives defined in the present invention are effective for the stabilization of peroxidase.

EXAMPLE 7

Various benzene derivatives were added to the peroxidase-bound antibody described in Example 4 in the amount of 3 mM and the enzyme stability was checked on Day 14. The results are shown in Table 7.

TABLE 7

| Benzene Derivatives | Stability (%) |
|---|---|
| p-hydroxyacetophenone | 99 |
| 2,4-dihydroxyacetophenone | 53 |
| p-hydroxybenzamide | 69 |
| p-hydroxyacetoanilide | 71 |
| p-nitrophenol | 66 |
| Not Added | 4 |

It can be seen from Table 7 that the benzene derivatives defined in the present invention are effective for the stabilization of peroxidase.

EXAMPLE 8

Various benzene derivatives were added to the peroxidase composition described in Example 1 and the enzyme stability on Day 7 was checked. The results are shown in Table 8.

TABLE 8

| Benzene Derivatives | Concentration (mM) | Stability (%) |
|---|---|---|
| Methyl p-hydroxybenzoate | 3 | 98 |
| n-propyl p-hydroxybenzoate | 0.3 | 92 |
| Ethyl 3,4-dihydroxybenzoate | 1 | 96 |
| Not Added | — | 17 |

As is apparent from Table 8, various benzene derivatives defined in the present invention are effective for the stabilization peroxidase.

EXAMPLE 9

To PBS containing 1 w/v% of BSA, horse radish peroxidase-bound anti-GT-II monoclonal antibody was added to a final concentration of 200 ng/ml. Hydroquinone was added to the solution as a stabilizer. Samples which further contained horse serum and/or sucrose were also prepared.

An aliquot (0.5 ml) of each sample was placed in a vial and was freezed at −40° C. The solvent was removed under reduced pressure and the sample was lyophilized. After the lyophilization, 0.5 ml of pure water was added and the enzyme activity was determined as in Example 1. The stability was expressed in terms of the percentage of the enzyme activity of the lyophilized sample to that of the sample which was not lyophilized. The results are shown in Table 9.

TABLE 9

| Additives | | | Stability (%) |
|---|---|---|---|
| Horse Serum | Sucrose | Hydroquinone Monomethyl Ethyl | |
| 5 wt % | 5 wt % | 5 mM | 100 |
| 5 wt % | — | 5 mM | 82 |
| — | 5 wt % | 5 mM | 85 |
| — | — | 5 mM | 71 |
| — | — | — | 45 |

It can be seen from Table 9, that the peroxidase composition which contains hydroquinone monomethyl ether has better stability than the composition which does not contain hydroquinone. Further, by adding the horse serum and/or sucrose, the stability is further promoted.

EXAMPLE 10

Anti-GT-II monoclonal antibody with a concentration of 10 μg/ml was fixed on a polystyrene beads at 4° C. overnight, and then the beads were blocked with 1 w/v % BSA-PBS. The resulting beads were then reacted with human ascite fluid at 21° C. overnight and the resultant was washed with PBS, followed by being allowed to react with a secondary antibody at 21° C. for 2 hours. As the secondary antibody, a composition containing 200 ng/ml of peroxidase-bound anti-GT-II monoclonal antibody, 1 w/v % of BSA, 5 w/v % of horse serum and 5 mM of the benzene derivative defined in the present invention in PBS, which was held at 4° C. or 37° C. for 1 week was employed. As the secondary antibody, compositions which did not contain the horse serum and/or the benzene derivative were also tested. After the reaction, the beads were washed with PBS and the enzyme activity of the beads was determined, which is defined as the activity of the secondary antibody. The stability of the secondary antibody is expressed in terms of the percentage of the activity of the secondary antibody held at 37° C. to that of the secondary antibody held at 4° C. Further, the enzyme activity of the secondary antibody was determined as in Example 4 and the enzyme stability was expressed in terms of percentage. The stability of the antibody is expressed in terms of percentage of the stability of the secondary antibody to the stability of the enzyme activity. The results are shown in Table 10.

TABLE 10

| Horse Serum | Benzene Derivatives (concentration) | Stability (%) | | |
|---|---|---|---|---|
| | | Enzyme | Sec. Ab* | Ab |
| 5 w/v % | Hydroquinone Monomethyl Ether (5 mM) | 100 | 96 | 96 |
| 5 w/v % | 2,4-dihydroxy Benzoic Acid (5 mM) | 97 | 93 | 96 |

TABLE 10-continued

| Horse Serum | Benzene Derivatives (concentration) | Stability (%) | | |
|---|---|---|---|---|
| | | Enzyme | Sec. Ab* | Ab |
| 5 w/v % | — | 83 | 32 | 39 |
| — | Hydroquinone Monomethyl Ether (5 mM) | 98 | 93 | 95 |
| — | 2,4-dihydroxy Benzoic Acid (5 mM) | 96 | 92 | 96 |
| — | — | 20 | 7 | 35 |

It is apparent from Table 10 that the antibody compositions containing the substituted benzene ring defined in the present invention have increased stability.

Although the invention was described based on the preferred embodiment thereof, it is apparent for those skilled in the art that various modifications may be made without departing the spirit and scope of the present invention.

We claim:

1. A peroxidase composition consisting essentially of:
   (a) a peroxidase or a peroxidase conjugated with an immunologically active substance;
   (b) a buffer;
   (c) a benzene derivative as a stabilizer; and
   (d) one of serum of animal, serum component, carbohydrate and water-soluble macromolecule,
wherein said benzene derivative is selected from the group consisting of:
   hydroquinone monomethyl ether, hydroquinone monoethyl ether, hydroquinone monophenyl ether, o-methoxyphenol, o-ethoxyphenol, 2,6-dimethoxyphenol, hydroquinone, N-methyl-p-hydroxyaniline, N,N-dimethyl-p-hydroxyaniline, N-(p-hydroxyphenyl)glycine, p-hydroxyacetophenone, 2,4-dihydroxyacetophenone, p-hydroxybenzophenone, p-hydroxybenzoic acid, m-hydroxybenzoic acid, o-hydroxybenzoic acid, 2,3-dihydroxybenzoic acid, 2,4-dihydroxybenzoic acid, 2,5-dihydroxybenzoic acid, 2,6-dihydroxy benzoic acid, 3,4-dihydroxybenzoic acid, 3,5-dihydroxybenzoic acid, 2,3,4-trihydroxybenzoic acid, 2,3,5-trihydroxybenzoic acid, 3,4,5-trihydroxybenzoic acid, 4-hydroxy-3-methoxybenzoic acid, 4-hydroxy-3,5-dimethoxybenzoic acid, 4-hydroxyphthalic acid, 2-hydroxyterephthalic acid, methyl p-hydroxybenzoate, ethyl p-hydroxybenzoate, n-propyl p-hydroxybenzoate, ethyl 3,4-dihydroxy benzoate, p-hydroxybenzamide, p-hydroxybenzoylethylamine, 1-naphthol-2-carboxylic acid, 3-naphthol-2-carboxylic acid, p-hydroxyacetoanilide, p-hydroxybenzenesulfinyl methane, p-hydroxybenzene sulfonamide, p-sulfonylphenol and p-nitrophenol.

2. An antibody composition consisting essentially of:
   (a) an antibody;
   (b) a buffer;
   (c) a benzene derivative as a stabilizer; and
   (d) one of serum of animal, serum component, carbohydrate and water-soluble macromolecule,
wherein said benzene derivative is selected from the group consisting of:
   hydroquinone monomethyl ether, hydroquinone monoethyl ether, hydroquinone monophenyl ether, o-methoxyphenol, o-ethoxyphenol, 2,6-dimethoxyphenol, hydroquinone, N-methyl-p-hydroxyaniline, N,N-dimethyl-p-hydroxyaniline, N-(p-hydroxyphenyl)glycine, p-hydroxyacetophenone, 2,4-dihydroxyacetophenone, p-hydroxybenzophenone, p-hydroxybenzoic acid, m-hydroxybenzoic acid, o-hydroxybenzoic acid, 2,3-dihydroxybenzoic acid, 2,4-dihydroxybenzoic acid, 2,5-dihydroxybenzoic acid, 2,6-dihydroxy benzoic acid, 3,4-dihydroxybenzoic acid, 3,5-dihydroxybenzoic acid, 2,3,4-trihydroxybenzoic acid, 2,3,5-trihydroxybenzoic acid, 3,4,5-trihydroxybenzoic acid, 4-hydroxy-3-methoxybenzoic acid, 4-hydroxy-3,5-dimethoxybenzoic acid, 4-hydroxyphthalic acid, 2-hydroxyterephthalic acid, methyl p-hydroxybenzoate, ethyl p-hydroxybenzoate, n-propyl p-hydroxybenzoate, ethyl 3,4-dihydroxy benzoate, p-hydroxybenzamide, p-hydroxybenzoylethylamine, 1-naphthol-2-carboxylic acid, 3-naphthol-2-carboxylic acid, p-hydroxyacetoanilide, p-hydroxybenzenesulfinyl methane, p-hydroxybenzene sulfonamide, p-sulfonylphenol and p-nitrophenol.

3. The peroxidase composition of claim 1, wherein said benzene derivative is selected from the group consisting of: hydroquinone monomethyl ether, hydroquinone monoethyl ether, hydroquinone monophenyl ether, o-methoxyphenol, o-ethoxyphenol, 2,6-dimethoxyphenol, hydroquinone, p-hydroxyacetophenone, p-hydroxybenzoic acid, 2,4-dihydroxybenzoic acid, 2,5-dihydroxybenzoic acid, 3,4-dihydroxybenzoic acid, 3,4,5-trihydroxybenzoic acid, 4-hydroxy-3,5-dimethoxybenzoic acid, methyl p-hydroxybenzoate, ethyl p-hydroxybenzoate, n-propyl p-hydroxybenzoate, ethyl 3,4-dihydroxybenzoate, 3-naphthol-2-carboxylic acid, m-hydroxybenzoic acid, 4-hydroxyphthalic acid, 2,4-dihydroxyacetophenone, and p-hydroxyacetoanilide.

4. The antibody composition of claim 2, wherein said benzene derivative is selected from the group consisting of: hydroquinone monomethyl ether, hydroquinone monoethyl ether, hydroquinone monophenyl ether, o-methoxyphenol, o-ethoxyphenol, 2,6-dimethoxyphenol, hydroquinone, p-hydroxyacetophenone, p-hydroxybenzoic acid, 2,4-dihydroxybenzoic acid, 2,5-dihydroxybenzoic acid, 3,4-dihydroxybenzoic acid, 3,4,5-trihydroxybenzoic acid, 4-hydroxy-3,5-dimethoxybenzoic acid, methyl p-hydroxybenzoate, ethyl p-hydroxybenzoate, n-propyl p-hydroxybenzoate, ethyl 3,4-dihydroxybenzoate, 3-naphthol-2-carboxylic acid, m-hydroxybenzoic acid, 4-hydroxyphthalic acid, 2,4-dihydroxyacetophenone, and p-hydroxyacetoanilide.

5. The peroxidase composition of claim 1, wherein the peroxidase is horseradish peroxidase.

6. The peroxidase composition of claim 1, wherein the immunologically active substance is selected from the group consisting of antigens, antibodies, haptens and protein A.

7. The peroxidase composition of claim 1, wherein said benzene derivative is added at a concentration of 0.005–500 mM.

8. The antibody composition of claim 2, wherein said benzene derivative is added at a concentration of 0,005–500 mM.

9. The peroxidase composition of claim 1, wherein said benzene derivative is added at a concentration of 0.01–50 mM.

10. The antibody composition of claim 2, wherein said benzene derivative is added at a concentration of 0.01–50 mM.

11. The antibody composition of claim 2, wherein said antibody is in the form of a conjugate with a labelling substance.

12. The antibody composition of claim 11, wherein the labelling substance is selected from the group consisting of radioisotopes, enzymes, fluorescent substances, luminescent substances, biotin, avidin, chelates, metal colloids and toxins.

13. The antibody composition of claim 12, wherein the enzyme is selected from the group consisting of alkaline phosphatase, peroxidase and β-galactosidase.

* * * * *